(12) United States Patent
Ohtake et al.

(10) Patent No.: US 6,350,577 B1
(45) Date of Patent: Feb. 26, 2002

(54) PLASMIDS ORIGINATING IN AMMONIA OXIDIZING BACTERIA AND USE OF THE SAME

(75) Inventors: Hisao Ohtake; Junichi Kato, both of Higashihiroshima; Yosuke Nakamura, Niihama, all of (JP)

(73) Assignee: Sumitomo Chemical Co., Ltd., Osaka (JP)

( * ) Notice: Subject to any disclaimer, the term of this patent is extended or adjusted under 35 U.S.C. 154(b) by 0 days.

(21) Appl. No.: 09/367,051

(22) PCT Filed: Feb. 4, 1998

(86) PCT No.: PCT/JP98/00454
   § 371 Date: Oct. 1, 1999
   § 102(e) Date: Oct. 1, 1999

(87) PCT Pub. No.: WO98/35050
   PCT Pub. Date: Aug. 13, 1998

(30)  Foreign Application Priority Data

Feb. 7, 1997 (JP) .............................. 9-025232
   Mar. 28, 1997 (JP) .............................. 9-077060

(51) Int. Cl.⁷ .......................... C12Q 1/02; C12N 15/00
(52) U.S. Cl. .................. 435/6; 435/320.1; 435/252.3; 435/29; 435/8; 435/25; 435/7.91
(58) Field of Search .......................... 435/320.1, 252.3, 435/6, 8, 25, 7.91, 29

(56)   References Cited

U.S. PATENT DOCUMENTS 5,900,362 A * 5/1999 Eberz et al. .................. 435/37

FOREIGN PATENT DOCUMENTS

JP   09224669   9/1997
   WO   94 24286   10/1994

OTHER PUBLICATIONS

Journal of Bacteriology, Jul. 1996; vol. 178, No. 13 pp. 3710–3714.

* cited by examiner

Primary Examiner—Rebecca E. Prouty
Assistant Examiner—Richard Hutson
(74) Attorney, Agent, or Firm—Birch, Stewart, Kolasch & Birch, LLP (57)   ABSTRACT

There are provided a plasmid characterized by having the nucleotide sequence of SEQ ID NO: 1, a plasmid characterized by having the nucleotide sequence of SEQ ID NO: 2, a plasmid characterized by having at least a part of the nucleotide sequences of SEQ ID NOs: 1 and 2 and further containing a selective marker gene, each plasmid being usable as a transformation vector for effecting gene manipulation in ammonia oxidizing bacteria, and transformants characterized in that they are obtained by transferring these plasmids into host organisms.

6 Claims, 3 Drawing Sheets

SEQUENCE LISTING

<160> NUMBER OF SEQ ID NOS: 2

<210> SEQ ID NO 1
<211> LENGTH: 1823
<212> TYPE: DNA
<213> ORGANISM: Nitrosomonas sp.

<400> SEQUENCE: 1

```
tgcgaaagca gtgaccacct ctactaacag gggggtcaca cccaacgggg acaatacgcc      60
gaaaacaaga cgggataagg cttcccaggt tgtttctgga aaaaagttt tttcgaaaag     120 ttgatcatgc taaaggcata aaacgatgag atttgactgg tatcaagcga ctatcgaagc     180
agattctttt tcggtgcttt ctgccgttga aaagctgggt agttttgtgg agcgggacga     240
caagattgcg aaacggtacc ggtacgatca gggttttgca gttcatcact acgaacgggg     300
tctcgttgct cgggtttttt ggggggggaa tgggaaaaat cctcatgcct tttcgagcgg     360
gcaagatact gatgcattcg tcgatctggt gcgttctgaa tggccagaca ggcacttggt     420
tactcggctt gactctgctg aggactttta tgaagaaggt gcctacgatc gcattctgag     480
ggtttctaag cgtatcgcta aagatcatcg tttgcagttt ccgaaaattg aggacgaatt     540
gaacccgatt gcaggacgaa cccagtatat cggtggcaag accagtgatt atcggggtcg     600
gctctatgag aagggctggg aagttgtcca gaagagcgct gagcgtcgcg gcggtttctg     660
```

-continued

| | |
|---|---|
| taccgaattt cgggggatgg ttgtcaatga gctgacaggg gaattatcg atccatcgat | 720 |
| ctgggtacgg cttgaacttc agggtaggcc gtctggagaa gaggccaggc gagccgcggc | 780 |
| cgcggcctct ccttccgaag catggacttt tacctcctgg tctaccgatc tggccaggga | 840 |
| agcgctatca cttgagatgg agcgcttcta tgtccgaact cgtaagttta gtaaggatga | 900 |
| gatggcgttc cgctggatgt gtaagcagta tggcgcaatg cttactcgcc gcttactttc | 960 |
| ggctggtgac tgggccgctg ttggtcgtga tcggcttg atgatcggtc agagtaagag | 1020 |
| ttcttcttct aacgactagc agaaaatctc atggatgggc gggtctggtt tatgccggtt | 1080 |
| ttccatgagt tttcgtcgcg ggttactccg taacgcttgc cttgttgcgc atcacaaca | 1140 |
| cccttcccc tttatggatg aacctcttca aggcttgccg ttcgttgaac tcttctatcg | 1200 |
| attttttgcct ggtactggct atacctacgt ttatcgtccc cgcactgttt ccgaattcaa | 1260 |
| agcattactc agtaacgact agcaggaaat atcgaggccg ccggacccgg tgttggtttt | 1320 |
| agggtaccgg cgcaacgcag aattttccgt cgcgggttac tccgtaacgg ttgccatgat | 1380 |
| gtgctatcaa tccccccttc ccctttacaa aacttttct tgtggtgcat caggtgatgc | 1440 |
| actatcatct ggtgcatctt cactgaggag agcatcatg ctaccacaaa accacgaatt | 1500 |
| accatcactc tgaccgatcg gcaatattcg gtattgcgca agatgtcgga ttccagcgga | 1560 |
| caacctatga gcggatttat cacagacctc attgaatcgg ccttgcctac tatggaaaag | 1620 |
| atgttgggca ctttccagca gattcgtagt tttcaggatg acaggaaaac gaaagttctt | 1680 |
| gctgccatgg atgaagctca agccgccttc gaacctctga ttaattactt gcttacgaat | 1740 |
| gctggaattg ctctcgatcg gggacttgaa gctgagcaga atcttttgag tgaggagcgc | 1800 |
| agcgagcgaa cgaaaaagaa ttc | 1823 |

<210> SEQ ID NO 2
<211> LENGTH: 1910
<212> TYPE: DNA
<213> ORGANISM: Nitrosomonas sp.

<400> SEQUENCE: 2

| | |
|---|---|
| gaattcttgc gtcgagctat tgatgatgct cttttccagag cggaggaacg tattaatgaa | 60 |
| ttattggagg atgaatgatg agcatgctta ccctgaacgg acagttttta aacgtatttg | 120 |
| atacaccgga gtcaacgaac cgaaaaaccg gggaagttat cccggctgct acacgtatcc | 180 |
| agatacaggc tgaaaatacc cttgagaacg gccagaaacg catcgaattg cttactttga | 240 |
| aggttgcccg tagaacccta tgaaaagctg attggatcgc ctgtgcgcgt tcctgttggc | 300 |
| gttttcgctt tcggcggttc agttgtttat tacgcgcttc aaacttccgg ggattctccc | 360 |
| cgagcttgag cgatgagcgc agcgatagag cgaaaagcgg gggagaattt cccctattc | 420 |
| ttgatactat agaactaaag cgcttatcca tttactggcg cgggtttcag ccggtgggat | 480 |
| tttcgcttca aatgagaagg agttgcaatt gtgaagggg aaaaactaaa cccctgtcc | 540 |
| gatgattgct tggcggctga atcggatcag ggggcctgcg gcgcttgccg tttgccgtta | 600 |
| aaaattgcgc gatactctag ggcacgctcg cttactttg agcatgctat ttttgcacgt | 660 |
| tctgccggtt tccacaagga agctaccaag ctggaaaact gctcggaata ccttcttttt | 720 |
| catcactact acaccgttga ccaggttcgg cttttttgcag cccgcttctg caaaaagcaa | 780 |
| cttctgtgcc ctatgtgcgc tattcggcgc ggttcgaaaa tgcttacatc gtatcttcaa | 840 |
| cggtatcaga tcgttactgc gtcacaatcc gatctgaagc cttatctggt gactttaacg | 900 |
| gttaagaatg gacctgattt acaggaacgt tttgtgcatt tgcgtaaagc tatgcgctcg | 960 |

-continued

```
atgttcaaat ctcgcagaaa tactaatcaa ggccagcgtt tcgttgagtt ttctaagtct   1020
gaaggtggtt ttcattcgat tgaggtaact aaccggggca acggctggca tcctcacgtg   1080
catatgatct ggttgtgtag ggaaaaacca gatcagtcgg ctctttcggc cgaatggcga   1140
gagattaccg gtgattctca cgtggttgac gtcaggcctt taactgatcc agttgacggc   1200
tttcttgagg tttgtaagta cgctcttaag ttctctgatc ttgagcctgg ccatcttttc   1260
gaagcgtaca agattttgtc tggttctcgc ctggtcgata gtcacggatt gatgagaggt   1320
gttcggttac cggatgatct tgtggatgaa cctcttcaag gcttgccgtt cgttgaactc   1380
ttctatcgat ttttgcctgg tactggctat acctacgttt atcgtccccg cactgtttcc   1440
gaattcaaag cattacgcag taacgactag caggaaatat cgaggccgcc ggacccggtg   1500
ttggttttag ggtaccggcg caacgcagat tttccgtcgc gggttacgcc gtaacggttg   1560
ccatgatgtg ctatcaatcc cccttcccc tttaccaaac aatccttttt gtgcgattat   1620
catccggtag ttatttttt ggattattgg agaatttcat gagcgatttt gataaatacc   1680
ttttgtatcg tgctttacac cgtaagttta cccggcctgt tgataagcct gatttggacg   1740
aagatgcggc tgctgcttat gccgaatata aggctgatca ggaagagtta gcggaagaat   1800
ggcgtgatgc tgtttaccct gatgagtaca ggaacatttg ctttaaagag agtcctgaat   1860
ttgctgatag attgactgat gtttgcgatg ctcttgacat aaaaaagcga            1910
```

PLASMIDS ORIGINATING IN AMMONIA OXIDIZING BACTERIA AND USE OF THE SAME

This application is the national phase under 35 U.S.C. § 371 of PCT International Application No. PCT/JP98/00454 which has an International filing date of Feb. 4, 1998, which designated the United States of America.

TECHNICAL FIELD

The present invention relates to plasmids derived from ammonia oxidizing bacteria and use of the same.

BACKGROUND ART

Ammonia oxidizing bacteria belonging to chemoautotrophic bacteria are microorganisms that obtain energy necessary for their life action only by biological reaction for oxidizing ammonia into nitrous acid. The ammonia oxidizing bacteria have an important role in the nitrogen cycle in nature. In addition, they are also important as microorganisms mediating the nitration process as the main reaction of nitrogen elimination in the biological treatment of human wastewater, domestic wastewater and industrial wastewater by the activated sludge process. In recent years, there has been a tendency to require an improvement in the efficiency of nitrogen elimination in the above biological treatment of wastewater from a viewpoint for the prevention of eutrophication in waters, and the function of ammonia oxidizing bacteria has drawn much attention. However, ammonia oxidizing bacteria exhibit extremely low speed in the oxidation of ammonia and in the growth because they cannot obtain energy by oxidative degradation of organic matter in contrast to the ordinary aerobic heterotrophic microorganisms. In addition, ammonia oxidizing bacteria are susceptible to the inhibition of growth by various organic chemical substances or metal elements, so that the degree of nitrogen elimination can easily be lowered when harmful matter is mixed in the influent raw wastewater during the biological treatment of wastewater.

As a means of overcoming the above defects of ammonia oxidizing bacteria, genetic recombination technique may be used, which is a technique of transferring an appropriate foreign gene fragment to ammonia oxidizing bacteria for improving the function of genes that code for enzymes associated with the ammonia oxidation and that exist on the chromosomes of ammonia oxidizing bacteria, followed by expression of these fragments, or transferring enzyme genes to ammonia oxidizing bacteria, which genes code for enzymes exhibiting detoxifying action against harmful substances to the ammonia oxidizing bacteria, followed by expression of these genes. No vector system, however, has been established so far for which ammonia oxidizing bacteria are used as a host organism; therefore, such genetic recombination technique cannot be carried out. There has been a great demand for the development of vector systems for which ammonia oxidizing bacteria are used as a host organism.

SUMMARY OF THE INVENTION

Under these circumstances, the present inventors have extensively studied. As a result, they have found out plasmids replicable in the cells of ammonia oxidizing bacteria, thereby completing the present invention.

Thus, the present invention provides:

1) A plasmid characterized by having the nucleotide sequence of SEQ ID NO: 1 (which plasmid is hereinafter referred to as the present plasmid S).

Figure 1:
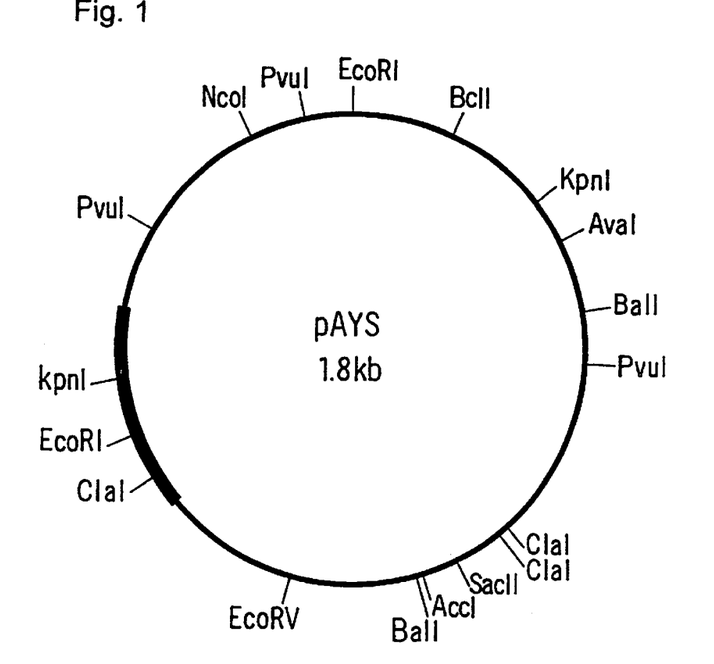
FIG. 1 is a diagram showing the restriction map of plasmid pAYS. The part represented by the thick line in the figure indicates a region highly homologous with plasmid pAYL.

2) A plasmid characterized by comprising about 1.8 kilobase pairs and being represented by the restriction map shown in FIG. 1.

3) A plasmid characterized by having the nucleotide sequence of SEQ ID NO: 2 (which plasmid is hereinafter referred to as the present plasmid L).

Figure 2:
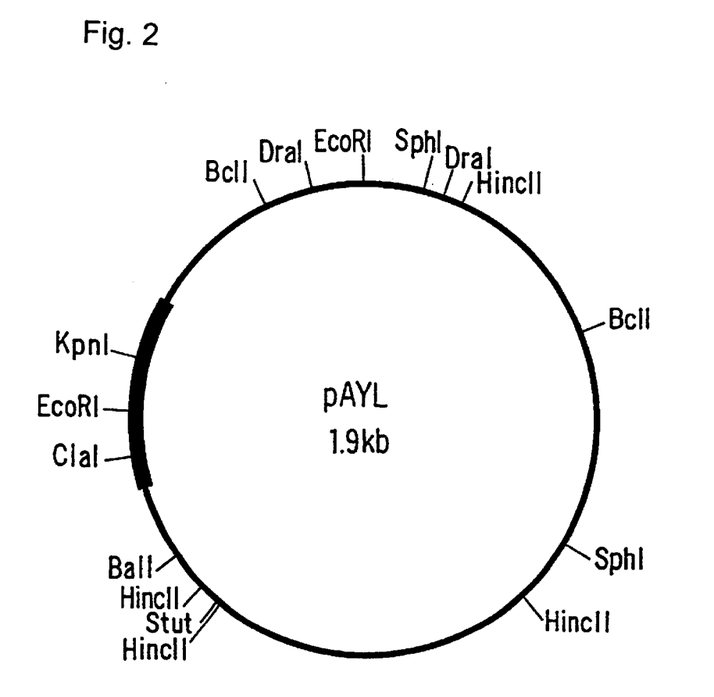
FIG. 2 is a diagram showing the restriction map of plasmid pAYL. The part represented by the thick line in the figure indicates a region highly homologous with plasmid pAYL.

4) A plasmid characterized by comprising about 1.9 kilobase pairs and being represented by the restriction map shown in FIG. 2.

5) A plasmid characterized by having at least a part of the nucleotide sequences of SEQ ID NOs: 1 and 2 and further containing a selective marker gene (which plasmid is hereinafter referred to as the present chimeric plasmid).

6) The plasmid according to item 5, characterized in that it is replicable in cells of either ammonia oxidizing bacteria or *Esherichia coli.*

Figure 3:
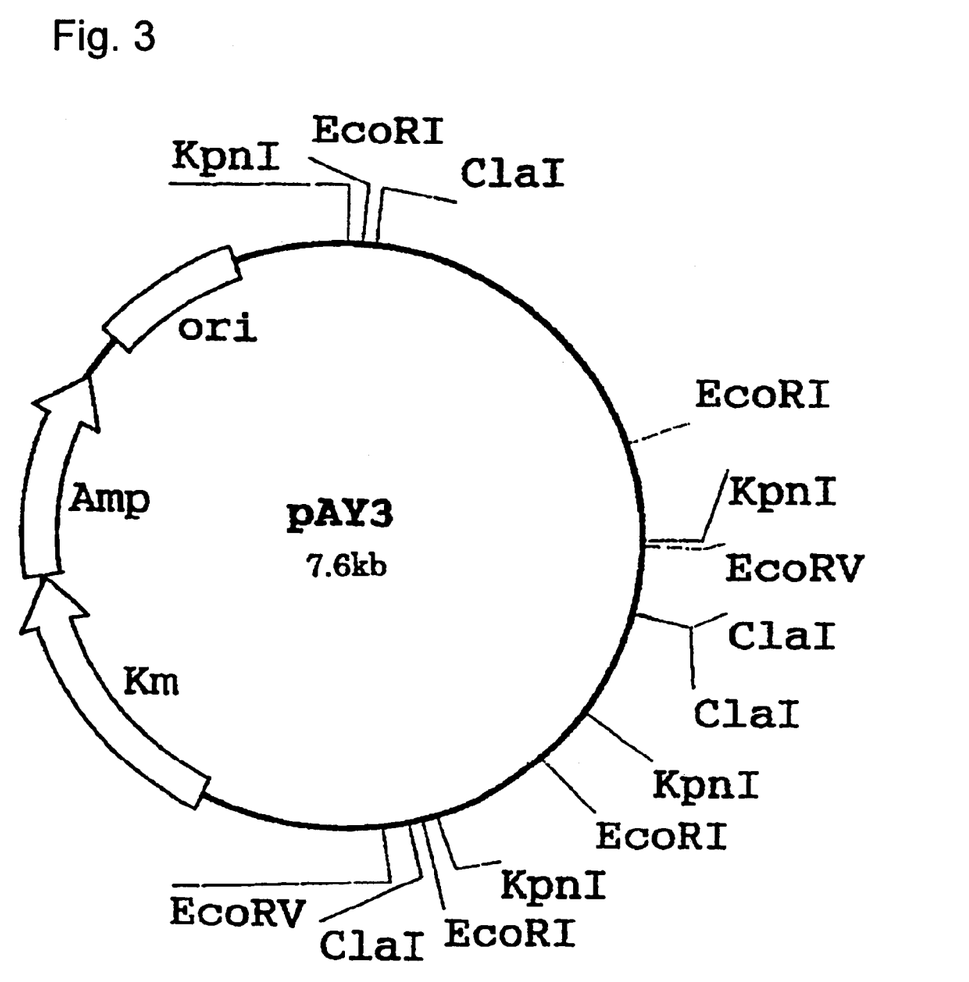
FIG. 3 is a diagram showing the restriction map of chimera plasmid pAY3. In the figure, Km indicates kanamycin resistance gene; Amp, ampicillin resistance gene; and ori, the replication origin of *Esherichia coil.*
Figure 4:
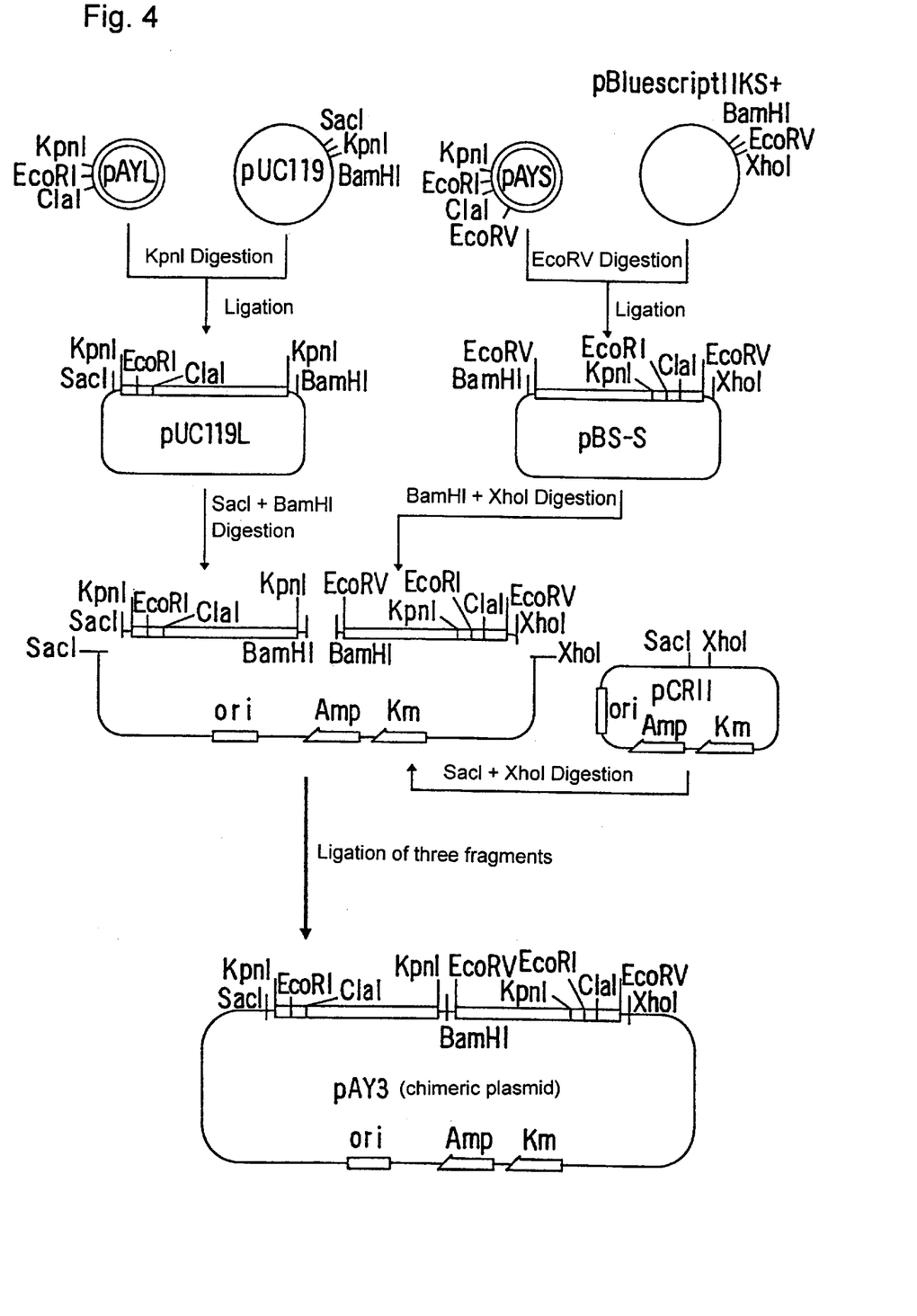
FIG. 4 is a diagram showing the procedures for the construction of chimera plasmid pAY3. In the figure, Km indicates kanamycin resistance gene; Amp, ampicillin resistance gene; and ori, the replication origin of *Esherichia coli.*

7) A plasmid characterized by comprising about 7.6 kilobase pairs and being represented by the restriction map shown in FIG. 3.

8) A transformant characterized in that it is obtained by transferring at least one plasmid according to any one of items 1 to 7 into a host organism.

9) A method for detecting ammonium ions in an aqueous solution, characterized in that a transformant obtained by transferring into ammonia oxidizing bacteria a plasmid according to any one of items 1 to 7, into which a luminescent organism derived gene coding for a protein associated with bioluminescence has been inserted, is brought into contact with both a sample aqueous solution and a substrate for the bioluminescence, and the bioluminescence of the said transformant is measured.

10) A method for preparing ammonia oxidation bacteria having resistance to nitrification inhibitory substances, characterized in that a plasmid according to any one of items 1 to 7, into which a gene coding for an enzyme that catabolizes nitrification inhibitory substances has been inserted, is transferred into ammonia oxidation bacteria to obtain a transformant.

11) A method for enhancing the ability of ammonia oxidizing bacteria to oxidize ammonia, characterized in that a plasmid according to any one of items 1 to 7, into which a gene coding for an enzyme associated with ammonia oxidation has been inserted, is transferred into ammonia oxidation bacteria to obtain a transformant.

DETAILED DESCRIPTION OF THE INVENTION

The following will describe the present invention in detail.

The present plasmids S and L are those which can be obtained from ammonia oxidizing bacteria belonging to the genus Nitrosomonas. More particularly, the present plasmid S may include, for example, plasmid pAYS comprising 1823 base pairs, wherein the whole nucleotide sequence is shown by SEQ ID NO: 1, and the present plasmid L may include, for example, plasmid pAYL comprising 1910 base pairs, wherein the whole nucleotide sequence is shown by SEQ ID NO: 2.

The present plasmids S or L can be prepared by the method for preparing plasmids, which is used in the ordinary genetic engineering technique as described, for example, by J. Sambrook, E. F. Fritsch, and T Maniatis, Molecular Cloning 2nd edition, Cold Spring Harbor Laboratory, 1989. More particularly, ammonia oxidizing bacteria belonging to the genus Nitrosomonas, which contain the present plasmid S or L, are first cultured, and from the bacterial cells obtained, the plasmids are extracted. As the method for culturing ammonia oxidizing bacteria belonging to the genus Nitrosomonas, there can be used an ordinary method for culturing ammonia oxidizing bacteria. In the culture medium, there can be used, for example, ammonium sulfate or ammonium chloride as ammonia sources; sulfates, phosphates or chlorides of potassium, sodium, magnesium, calcium or iron, as inorganic salts; and organic salts. Specific examples are potassium monohydrogenphosphate, potassium dihydrogenphosphate, sodium chloride, sodium hydrogencarbonate, disodium hydrogenphosphate, magnesium sulfate heptahydrate, calcium chloride dihydrate, calcium carbonate, ferrous sulfate heptahydrate, and iron ethylenediaminetetraacetate trihydrate. As other inorganic elements, for example, sulfates or chlorides of copper, cobalt, molybdenum, manganese or zinc can also be added in slight amounts. Specific examples are copper sulfate pentahydrate, cobalt chloride hexahydrate, sodium molybdate dihydrate, manganese chloride tetrahydrate, manganese sulfate tetrahydrate, and zinc sulfate heptahydrate. The growth of ammonia oxidizing bacteria involves the oxidation into nitrous acid of ammonia contained in the medium, so that the pH of the culture liquid is lowered with the lapse of time. At that time, to prevent the pH of the culture liquid from being lowered, chemical substances having buffer action and being harmless to the growth of ammonia oxidizing bacteria can also be added to the culture medium in advance. The chemical substance which can be added may include, for example, HEPES (N-2-hydroxyethyl-piperazin-N'-2-ethanesulfonic acid).

Culturing is carried out according to the ordinary method for culturing strict anaerobic bacteria. Any type of liquid culture can be used, such as test tube shaken cultures, reciprocating shaken cultures, rotary shaken cultures and cultures in jar fermenters. The incubation temperature may be suitably altered within a range in which ammonia oxidizing bacteria can be grown, but it is, for example, in the range of about 20° C. to about 35° C., preferably about 25° C. to about 30° C. The pH of a culture medium has a suitable range extending from neutral to slightly alkaline points and is, for example, preferably about 7 to about 8. If necessary, to keep the pH in the suitable range, a solution of an alkaline substance such as about 5% to about 10% by weight of sodium carbonate or about 1N sodium hydroxide can suitably be added dropwise to the medium. The incubation time may vary with various conditions, but it is usually preferred to be about 5 days to about 20 days. The above microorganism is difficult to confirm the growth, for example, by measuring the turbidity of the culture liquid through visual observation or with a turbidimeter or other means because the speed of growth and the yield of bacterial cells are low, in general. It is, therefore, preferred that the growth is confirmed by detecting the formation of nitrous acid in the culture liquid using ion chromatography or other techniques. In the case of a solid culture, it is preferred that purified polysaccharides such as GELLAN GUM (Wako Pure Chemicals Industries, Ltd.) are used as a solidifying agent for the medium. Agar, which is widely used, in general, may often contain impurities, and therefore, when agar is used, the colony of the above microorganism will not be formed, or even if formed, it is very small in size, making it difficult to handle the bacterial cells. The bacterial cells of the above microorganism thus grown are collected by centrifugation, and the present plasmid S or L can be then obtained according to an ordinary method for extracting plasmids from bacteria, such as alkaline-SDS method, as described, for example, by H. C. Birnboim and J. Doly, Nucleic Acids Research, 7, 1513–1523 (1979).

The plasmid structure can be determined by any method according to the ordinary genetic engineering techniques. Various restriction fragments of the present plasmid S or L are inserted into plasmid vectors for which *Esherichia coli* is used as a host organism, followed by transformation of *Esherichia coli*, from which the plasmid vector DNA is extracted and then subjected to a commercially available sequencer. The nucleotide sequence determined can be used for the preparation of a restriction map, for comparison with known nucleotide sequences, or other studies, using commercially available software of gene analysis for use in personal computers. Furthermore, according to the above comparison method, for example, some regions with high homology between the plasmids can be found, and these regions can also be utilized for the construction of transformation vectors. The regions with high homology between the plasmids may include, when the nucleotide sequences of pAYS as the present plasmid S and pAYL as the present plasmid L are examined by comparison, for example, the 262 base pair region of pAYS extending from the 1152nd site to the 1413th site in SEQ ID NO: 1 and the 261 base pair region of pAYL extending from the 1340th site to the 1600th site in SEQ ID NO: 2.

The ammonia oxidizing bacteria belonging to the genus Nitrosomonas, which contain the present plasmid S or L, may include, for example, a bacterium isolated from activated sludge by the method as described below in Example 1 and designated Nitrosomonas sp. ENI-11, which was deposited under the Budapest treaty as FERM BP-5774 (date of the original deposit, Dec. 18, 1996) at the National Institute of Bioscience and Human Technology, Agency of Industrial Science and Technology, 1–3, Higashi 1 chome, Tsukuba-shi, Ibaraki-ken, Japan. The bacteriological characteristics of Nitrosomonas sp. ENI-11 are as follows:

(a) Morphology

Cell form and dimensions

| Form: | Rods (short rod bacteria) |
|---|---|
| Dimensions: | 0.5 $\mu$m to 0.7 $\mu$m × 1.0 $\mu$m to 1.4 $\mu$m |

| | |
|---|---|
| Gram-staining: | negative |
| Motility: | none |

(b) Growth
Production of nitrous acid from ammonia: +
Production of nitric acid from nitrous acid: −
Growth on a nutrient medium such as CGY medium: −

| | |
|---|---|
| Requirement for oxygen: | strict aerobic |
| Optimal growth temperature range: | 28° C. to 32° C. |
| Optimal growth pH range: | 7.5 to 8.0 |

(c) Other characteristics
GC content: 50%

The present inventors searched these characteristics in the Bergey's Manual of Systematic Bacteriology (1984) and determined that the bacterial strain is reasonably assigned to the genus Nitrosomonas.

A chimeric plasmid can be prepared, which has at least a part of the nucleotide sequences of SEQ ID NOs: 1 and 2, respectively, contained in the present plasmids S and L, and which further contains a selective marker gene fragment (which plasmid is hereinafter referred to as the present chimeric plasmid). The present chimeric plasmid may include, for example, a plasmid containing the nucleotide sequence of SEQ ID NO: 1 and a selective marker gene, a plasmid containing the nucleotide sequence of SEQ ID NO: 2 and a selective marker gene, and a plasmid containing the nucleotide sequences of SEQ ID NOs: 1 and 2, and a selective marker gene. A specific example is a plasmid comprising about 7.6 kilobase pairs and being represented by the restriction map shown in FIG. 3.

The selective marker gene to be contained in the present chimeric plasmid refers to a gene functionable as a marker that makes it possible to detect the presence of the plasmid in a host organism. The selective marker can be utilized, for example, for screening the plasmid transferred host organisms from the non-transferred host organisms. The selective marker gene is not particularly limited, so long as it is functionable as a selective marker in a host organism into which the present chimeric plasmid is to be transferred. There can be used, for example, a gene conferring drug resistance on the host organism or a gene compensating for the nutrient requirement of the host organism. Specific examples of the selective marker gene are antibiotic resistance genes derived from various commercially available vectors, such as kanamycin resistance gene, ampicillin resistance gene, tetracycline resistance gene, neomycin resistance gene and chloramphenicol resistance gene; amino acid requirement compensating genes such as tryptophan requirement compensating gene and histidine requirement compensating gene; and nucleic acid requirement compensating genes such as uracil requirement compensating gene. The present chimeric plasmid which is to be transferred into two or more kinds of host organisms may contain on the same plasmid two or more kinds of genes functionable as the selective marker in each of the host organisms, or may contain only one kind of gene functionable as the selective marker in both the host organisms. In addition, for example, when two kinds of the present chimeric plasmids are both transferred into a host organism, it is convenient for the screening of transformants, if two kinds of chimeric plasmids to be used for the transfer contain different selective marker genes.

The present chimeric plasmids can be prepared according to the ordinary genetic engineering techniques. For example, to prepare a plasmid containing the nucleotide sequence of SEQ ID NO: 1 or 2 and a selective marker gene, the present plasmid S or L, and the selective marker gene containing *Esherichia coli* vector are digested with appropriate restriction enzymes, both the fragments are combined by ligation, and the resulting construct is transformed into *Esherichia coli,* from which the plasmid DNA is extracted. Furthermore, for example, to prepare a plasmid containing the nucleotide sequences of SEQ ID NOs: 1 and 2, and a selective marker gene, the present plasmids S and L, and the selective marker gene containing *Esherichia coli* vector are digested with appropriate restriction enzymes, these three fragments are combined by ligation, and the resulting construct is transformed into *Esherichia coli,* from which the plasmid DNA is extracted. For the selective marker gene containing *Esherichia coli* vector, there can be used, for example, commercially available plasmid vectors for *Esherichia coli.*

The transfer of the present plasmid S, L, or the present chimeric plasmid into a host organism according to the ordinary genetic engineering techniques achieves the preparation of a transformant. More particularly, for example, the present plasmid S, L, or the present chimeric plasmid can be transferred into ammonia oxidizing bacteria, a typical example of which is *Nitrosomonas europaea,* by the electroporation method as described by N. G. Hommes, L. A. Sayavedra-Soto, and D. J. Arp, Journal of Bacteriology, 178, 3710–3714 (1996) to prepare a transformant. The transfer of plural kinds of the above plasmids into ammonia oxidizing bacteria may also be used for the preparation of a transformant. Furthermore, the transfer of the present chimeric plasmid into *Esherichia coli* by the calcium chloride treatment as described by D. Hanahan, Journal of Molecular Biology, 166, 557–580 (1983) can also achieve the preparation of a transformant.

The present chimeric plasmid can be used as a vector for the expression of a trait in ammonia oxidizing bacteria, which trait is not inherently possessed by the ammonia oxidizing bacteria, by incorporating a foreign gene into the vector and transferring the vector thus obtained into the ammonia oxidizing bacteria as a host organism. A plasmid is constructed by inserting, for example, genes coding for proteins associated with the bioluminescence of luminescent bacteria such as *Vibrio fischeri,* and gene fragments such as lux operon as described, for example, by J. H. Devine, C. Countryman, and T. O. Baldwin, Biochemistry, 27, 837–842 (1988) into the present chimeric plasmid. The plasmid thus obtained can be used for transforming ammonia oxidizing bacteria such as *Nitrosomonas europaea* to express the trait of bioluminescence in the transformant.

The recombinant thus obtained can be used for the detection and determination of ammonium ions in a water sample by bringing the transformant into contact with the water sample. The transformant may be used as such after the growth in suspension culture, or as those fixed and carried on an appropriate support (in which case is hereinafter referred to as the immobilized bacterial cells) by microorganism carrying and immobilization techniques such as entrapment immobilization as described, for example, in "Biseibutsu-koteika-ho ni yoru Haisui-shori (translated title: Wastewater Treatment by Microorganism Immobilization Method)", Sudo Ryuichi ed., published by Sangyo-yosui Chosa-kai (1988). In both cases, some enzymes of the electron transport system in the bacterial cells function using as a substrate protons ($H^+$) that are formed from ammonium ions by the ammonia oxidizing action inherently possessed by the transformant, and an enzyme (i.e., luciferase) produced by the expression of the lux gene transferred into the transformant functions in conjugation with the above electron transport system and acts on the substrate to cause luminescent reaction. The measurement of light amount or luminous intensity at that time using a photodetector such as a luminometer makes it possible to attain the detection and determination of ammonium ions. Furthermore, when ammonium ions are present in a water sample to such a degree that they can be detected by the bioluminescence of the above transformant, if chemical substances that inhibit the nitrifying function of ammonia oxidizing bacteria (which chemical substances are hereinafter referred to as the nitrification inhibitory substances) are also present in the water sample, the luminescent reaction of the above transformant is inhibited depending upon the concentration of the nitrification inhibitory substances. Therefore, the nitrification inhibitory substances in a sample can also be detected and determined by using a water sample that has been found to contain no nitrification inhibitory substances as a control, bringing the control and a test sample into contact with the culture liquid or immobilized bacterial cells of the above transformant, measuring the bioluminescence of the transformant, and then comparing the measured values for the control and the test sample. A specific example is the test of raw wastewater for nitrification inhibitory substances in the biological treatment (e.g., activated sludge method or biological membrane method) of sewage, industrial wastewater or the like.

The above transformant can also be used to make a sensor for ammonium ions by immobilizing the transformant in such a manner as a probe, for example, according to the method as described by M. Hikuma, T. Kubo, and T. Yasuda, Analytical Chemistry, 52, 1020–1024 (1980), and connecting the probe, for example, with an optical fiber cable, to a luminometer as described above. The determination of ammonium ion concentration using such a sensor makes it possible to carry out the measurement of ammonia and/or nitrification inhibitory substances without collecting a test water sample, for example, even in the system of running water. For example, a wastewater watching system can be constructed, in which nitrification inhibitory substances in wastewater flowing into a control tank equipped at the foregoing stage of a tank for wastewater treatment with activated sludge are detected by making use of the above transformant to give instruction signals such as closing of inflow valves and temporary storage of toxic substance containing wastewater in a side pit.

The resistance to nitrification inhibitory substances can be conferred on transformants by inserting fragments of enzyme genes responsible for the catabolization or detoxification of nitrification inhibitory substances into the present chimeric plasmid and transforming ammonia oxidizing bacteria such as *Nitrosomonas europaea* with the plasmid. Examples of the nitrification inhibitory substances are described, for example, by C. Bedard et al., Microbiological Reviews, 53, 68–84 (1989) and D. J. W. Blum et al., Research Journal of Water Pollution Control Federation, 63, 198–207 (1991). Among them, examples of the substances for which the enzymes associated with the catabolization or detoxification of these substances by microorganisms have already been elucidated to the level of genes coding for these enzymes are cyanides, phenol, toluene, xylene, cresol, and aniline. The transformation of ammonia oxidizing bacteria is achieved with a plasmid that is obtained by inserting enzyme genes responsible for the catabolization or detoxification of these nitrification inhibitory substances, such as xylene catabolization gene xyl operon described by T. Nakazawa, S. Inouye, and A. Nakazawa, Plasmids in Bacteria, 415, Plenum Publishing (1985), solely or in combination into the present chimeric plasmid. The transformant thus obtained gets resistance to each nitrification inhibitory substance. For example, in the process of biological treatment of industrial wastewater that may contain nitrification inhibitory substances as described above, the addition of culture liquid or bacterial cells (including those processed by entrapment immobilization or other techniques) of the above transformant to a tank for wastewater treatment with activated sludge makes it possible to catabolize or detoxify the nitrification inhibitory substances in the tank for wastewater treatment, to control the lowering of the nitrification function of activated sludge in the tank for wastewater treatment, and to stabilize the performance of nitrogen elimination from the water to be treated.

The ammonia oxidizing ability of host organisms can be enhanced by inserting fragments of genes coding for enzymes associated with the ammonia oxidation, such as ammonia monooxygenase (amo) and hydroxylamine oxide reductase (hao), into the present chimeric plasmid, transforming ammonia oxidizing bacteria such as *Nitrosomonas europaea* with the plasmid, and increasing the number of copies of the amo and hao genes in the host organisms. More particularly, the amo and hao genes of Nitrosomonas sp. ENI-11 or other ammonia oxidizing bacteria are inserted into the present chimeric plasmid, which is used for the transformation of ammonia oxidizing bacteria (e.g., Nitrosomonas sp. ENI-11). The transformant thus obtained has an increased number of copies of the respective genes as compared with the ordinary ammonia oxidizing bacteria having 2 copies of the amo gene and 3 copies of the hao gene on the chromosome. The expression of these copies can exhibit high activity for ammonia oxidation. The nitrification of wastewater can be accelerated by constructing a reactor for preparing a culture of the transformant, and subjecting domestic wastewater, human wastewater or industrial wastewater, containing a high concentration of nitrogen in the form of ammonia, as a substrate to the reactor. In the reactor, the transformant may be used as those grown by suspension culture or may also be used as immobilized bacterial cells that have been grown in advance. The wastewater thus treated in the reactor may be fed to the ordinary process of wastewater treatment with activated sludge involving an anaerobic step and then subjected to the nitrification or denitrification reaction, so that the nitrogen concentration in the treated water can be reduced. Furthermore, the addition of culture liquid or bacterial cells (including those processed by entrapment immobilization or other techniques) of the above transformant to the ordinary tank for wastewater treatment with activated sludge makes it possible to accelerate the nitrification in the tank for wastewater treatment and to reduce the nitrogen concentration in the treated water.

The following working examples are provided for making and using the present invention; however, the present invention is not limited to these working examples.

EXAMPLE 1
(Example of Isolation of Bacterial Cells)

Activated sludge was collected from a chemical factory and added in a dry weight of 10 mg to 100 mL of medium containing 0.2% by weight of ammonium sulfate, 0.05% by weight of potassium dihydrogenphosphate, 0.005% by weight of magnesium sulfate heptahydrate, 0.0004% by weight of calcium chloride dihydrate and 0.00001% by weight of iron ethylenediaminetetraacetate trihydrate, and having been adjusted to pH 8 by the addition of 1N sodium hydroxide solution (which medium is hereinafter referred to as the AL medium). In a 500-mL Erlenmeyer flask with a silicone stopper was incubated a rotary shaken culture at a speed of about 120 rotations per minute. The incubation temperature was kept at 30° C. Every one or two days from the 4th day after the start of incubation, the pH of the medium was measured with a pH meter and the concentrations of ammonium and nitrite ions in the medium were determined by ion chromatography. Every time the pH became less than 7, the medium was adjusted to pH 8 by the addition of 1 N sodium hydroxide solution. These procedures were repeated. Since on the 10th day of incubation, the concentration of nitrite ions in the medium exceeded 50 mg/L, a part of the culture liquid was transferred to a fresh AL medium (the amount of culture liquid transferred was set at the 1/10-fold level relative to the fresh medium volume). The same procedures for incubation and transfer were repeated four times, and a subculture was then prepared on a medium containing 0.2% by weight of ammonium sulfate, 0.05% by weight of sodium hydrogencarbonate, 0.05% by weight of potassium monohydrogenphosphate, 0.005% by weight of magnesium sulfate heptahydrate, 0.0005% by weight of calcium chloride dihydrate, 0.0005% by weight of iron ethylenediaminetetraacetate trihydrate, 0.0002% by weight of manganese sulfate tetrahydrate, 0.00001% by weight of copper sulfate, 0.00001% by weight of zinc sulfate heptahydrate, 0.000005% by weight of sodium molybdate dihydrate and 0.0000001% by weight of cobalt chloride hexahydrate, and having been adjusted to pH 8 by the addition of 50 mM HEPES buffer solution (which medium is hereinafter referred to as the modified Alexander medium), followed by subculture for four generations. At such a stage that sufficient accumulation of ammonia oxidizing bacteria was considered, plate cultures were prepared. More particularly, a part of the culture liquid was diluted with a physiological salt solution and spread over plate media that had been obtained by solidifying medium liquid having the same composition as the above liquid medium (i.e., modified Alexander medium) with 1% by weight of GELLAN GUM, followed by incubation at 30° C. Colonies of the microorganism beginning to form after about 10 days were collected with platinum wire and transferred to the same liquid medium as described above, which afforded Nitrosomonas sp. ENI-11.

EXAMPLE 2
(Example of Culture Preparation of Bacterial Cells)

First, 300 mL of modified Alexander medium was put in a 2000-mL Erlenmeyer flask with a silicone stopper, and 5 to 50 mL of the culture liquid of Nitrosomonas sp. ENI-11 was added to the flask, in which case the culture liquid had been previously prepared on media having the same composition as the above liquid medium. The flask was incubated at 28° C. for 5 days on a rotary shaker operating at a speed of about 120 to about 160 strokes per minute, which afforded culture liquid of bacterial cells.

EXAMPLE 3
(Example of Plasmid Extraction)

The bacterial cells were collected from the above culture liquid by centrifugation at 10,000 rpm for 10 minutes and then suspended in 0.1 mL of TE solution (10 mM trishydroxyemthylaminomethane, pH 8, 1 mM disodium ethylenediaminetetraacetate). The suspension was transferred to a 1.5-mL microcentrifuge tube (Eppendorf tube), and 0.4 N sodium hydroxide solution and 2% by weight sodium dodecylsulfate solution were added in volumes of 0.1 mL, which was gently shaken and left undisturbed on ice for 5 minutes. Further, 0.15 mL of 3M potassium acetate solution (pH 5.2) was added, and the mixture was gently shaken and left undisturbed on ice for 5 minutes. The microcentrifuge tube was centrifuged at 15,000 rpm for 5 minutes, and the supernatant was transferred to another microcentrifuge tube. Then, 0.45 mL of TE solution saturated phenol/chloroform (volume ratio, 1/1) was added, and the mixture was stirred with gentle inversion of the tube. The microcentrifuge tube was centrifuged again at 15,000 rpm for 5 minutes, and the supernatant was transferred to another microcentrifuge tube. Then, 0.45 mL of TE solution saturated phenol/chloroform (volume ratio, 1/1) was added, and the mixture was stirred for 5 minutes with gentle inversion of the tube. The microcentrifuge tube was further centrifuged at 15,000 rpm for 5 minutes, and the supernatant was transferred to another microcentrifuge tube. Then, 0.9 mL of 99.5% ethanol was added, and the mixture was laced on ice for 10 minutes. The microcentrifuge tube was centrifuged at 15,000 rpm for 5 minutes, after which the supernatant was discarded and the precipitate was washed with 70% ethanol. After drying in vacuo, the precipitate (plasmid DNA) was dissolved in 0.015 mL of TE solution. In such a manner, the plasmid DNA was obtained.

EXAMPLE 4
(Example of Plasmid Cloning and DNA Sequence Determination for Nucleic Acid)

The plasmid DNA obtained in Example 3 was treated with one or two of the restriction enzymes, Eco RI, Bam HI, Sac I, Sph I, Bal I and Kpn I, available from Takara Shuzo Co., Ltd. or Boehringer Mannheim Corporation, by incubation at 37° C. for 1 hour in the case of full digestion or for 10 seconds in the case of partial digestion. The solutions after the restriction digestion were subjected to electrophoresis in 1.0% agarose gels at 100 V to separate the respective restriction DNA fragments. The gels were then immersed in 0.5 mg/L ethidium bromide solution for 15 minutes, followed by detection of the DNA fragments using an ultraviolet irradiator. The portions of the gels containing the desired DNA fragments were cut out with a razor, and the DNA fragments were isolated and purified from the gels using the GENE CLEAN II KIT available from BIO101, Inc. The respective restriction DNA fragments were ligated to cloning vector plasmids of *Esherichia coli*, pUC118, pUC119 (Takara Shuzo Co., Ltd.) and pBluescript II SK (Stratagene, Inc.), using the Ligation high kit available from Toyobo Co., Ltd. The conditions of treatment were set at 16° C. for 30 minutes. The cloning vector plasmids containing the respective restriction DNA fragments ligated were used for the transformation of *Esherichia coli* MV1184 by the competent sell method involving the calcium chloride treatment. The insertion of the desired DNA fragments into the cloning vector plasmids was confirmed by the technique in which the formation of white colonies by lack of β-galactosidase activity on the agar plate cultures of the transformed strains was used for distinction. According to the ordinary method for the preparation of *Esherichia coli* cultures, overnight cultures of the white colonies were prepared, from which the cloning vector plasmids containing the respective restriction DNA fragments ligated were extracted and confirmed for the insertion of the fragment by restriction treatment and electrophoresis. The sequence determination for nucleic acid of the inserted fragments was carried out using ALFred DNA Sequencer available from Pharmacia Biotech A B. Based on the nucleotide sequences of the inserted fragments determined, the restriction maps of the plasmids were prepared using the DNASIS V2.0 gene analysis software available from Takara Shuzo Co., Ltd. (FIGS. 1 and 2). The comparison of the nucleotide sequences of two plasmids (designated pAYS and pAYL, respectively) determined revealed that the region of 262 base pairs extending from the 1151st site to the 1412th site in SEQ ID NO: 1 and the region of 261 base pairs extending from the 1339th site to the 1599th site in SEQ ID NO: 2 have high homology.

EXAMPLE 5
(Construction of the Present Chimeric Plasmids)

The plasmid pAYL, of which nucleotide sequence was determined in Example 4, and plasmid pUC119 (Takara Shuzo Co., Ltd.) were digested with the restriction enzyme Kpn I (Takara Shuzo Co., Ltd.) separately, and the both were ligated together using the Ligation high kit available from Toyobo Co., Ltd. The conditions of ligation were set at 16° C. for 30 minutes. Using the ligation mixture, *Esherichia coli* MV1184 as a host organism was transformed by the competent cell method involving the calcium chloride treatment. The insertion of the desired DNA fragment of plasmid pAYL into the cloning vector plasmid pUC119 was confirmed by the technique in which the formation of white colonies by lack of β-galactosidase activity on the agar plate cultures of the transformed strains was used for distinction. According to the ordinary method for the preparation of *Esherichia coli* cultures, overnight cultures of the white colonies were prepared, from which the plasmid DNA was extracted and confirmed for insertion of the fragment by restriction treatment and electrophoresis. The plasmid obtained (hereinafter referred to as pUC119L) was digested with restriction enzymes Sac I and Bam HI (Takara Shuzo Co., Ltd.), and the solution after the restriction treatment was subjected to electrophoresis in a 1.0% agarose gel at 100 V to separate the restriction DNA fragment. The gel was then immersed in 0.5 mg/L ethidium bromide solution for 15 minutes, followed by detection of the DNA fragment using an ultraviolet irradiator. The portion of the gel containing the DNA fragment having plasmid pAYL (about 1.9 kb, designated DNA fragment L) was cut out with a razor, and the DNA fragment was isolated and purified from the gel using the GENE CLEAN II KIT available from Funakoshi.

The plasmid pAYS, of which nucleotide sequence was determined in Example 4, and plasmid pBluescript II KS+ (Toyobo Co., Ltd.) were digested with the restriction enzyme Eco RV (Takara Shuzo Co., Ltd.) separately, and the both were ligated together using the Ligation high kit available from Toyobo Co., Ltd. The conditions of ligation were set at 16° C. for 30 minutes. Using the ligation mixture, *Esherichia coli* MV1184 as a host organism was transformed by the competent cell method involving the calcium chloride treatment. The insertion of the desired DNA fragment of plasmid pAYS into the cloning vector plasmid pBluescript II KS+ was confirmed by the technique in which the formation of white colonies by lack of β-galactosidase activity on the agar plate cultures of the transformed strains was used for distinction. According to the ordinary method for the preparation of *Esherichia coli* cultures, overnight cultures of the white colonies were prepared, from which the plasmid DNA was extracted and confirmed for the insertion of the fragment by restriction treatment and electrophoresis. The plasmid obtained (hereinafter referred to as pBS-S) was digested with restriction enzymes Xho I and Bam HI (Takara Shuzo Co., Ltd.), and a DNA fragment having plasmid pAYS (about 1.8 kb, designated DNA fragment S) was isolated and purified in the same manner as described above in the case of pUC119L.

Furthermore, plasmid pCRII (Invitrogen Corp.) having kanamycin resistance gene and ampicillin resistance gene was digested with restriction enzymes Sac I and Xho I (Takara Shuzo Co., Ltd.), and a DNA fragment having plasmid PCRII (about 3.9 kb, designated DNA fragment C) was isolated and purified in the same manner as described above in the case of pUC119L.

DNA fragments L, S and C obtained (each in about 0.5 μg) were mixed and ligated together using the Ligation high kit available from Toyobo Co., Ltd. The conditions of ligation were set at 16° C. for 30 minutes. The ligation mixture used for the transformation of *Esherichia coli* MV1184 as a host organism by the competent cell method involving the calcium chloride treatment. A culture of the transformed *Esherichia coli* was grown on an agar plate containing ampicillin (100 mg/L) for screening the transformant. According to the ordinary method for the preparation of *Esherichia coli* cultures, an overnight culture of the transformant colonies was prepared, from which the plasmid DNA was extracted and confirmed for the plasmid structure by restriction treatment and electrophoresis. The plasmid with such a structure in which DNA fragments L, S and C are ligated together (FIG. 3) was designated chimeric plasmid pAY3.

EXAMPLE 6
(First Examples of Transformation of Ammonia Oxidizing Bacteria Using the Present Chimeric Plasmids)

Using the present chimeric plasmids as vectors, the transformation of ammonia oxidizing bacteria ENI-11 belonging to the genus Nitrosomonas is carried out. Two chimeric plasmids are prepared (hereinafter referred to as chimeric plasmids pAYS and pAYL, respectively). The former is obtained by ligating an Eco RV digestion DNA fragment (size, 3932 base pairs) of plasmid pCRII (Invitrogen Corp.) having kanamycin resistance gene and ampicillin resistance gene to the restriction Eco RV site (i.e., the 991st site in SEQ ID NO: 1) of pAYS obtained in Example 4, using the above Ligation high kit; and the latter is obtained by ligating a Kpn I digestion DNA fragment (size, 2676 base pairs) of plasmid pHSG298 (Takara Shuzo Co., Ltd.) having kanamycin resistance gene at the restriction Kpn I site (i.e., the 1515th site in SEQ ID NO: 2) of pAYL obtained in Example 4, using the above Ligation high kit. A shaken culture of ammonia oxidizing bacteria ENI-11 as a host organism is grown in 1000 mL of a medium for 38 to 40 hours according to Example 2, and the bacterial cells are collected by centrifugation and washed three times with sterilized water, which are then suspended in 0.4 mL of sterilized water. To this is added 0.01 mL of TE solution containing 1 μg of each DNA of chimeric plasmids pAYS and pAYL, and these mixtures are transferred in the whole volume to cuvettes with 2 mm gaps. A voltage is applied to the cuvettes using an apparatus for electroporation, Electro Cell Manipulator 600 available from BTX. The conditions of voltage application are set at a voltage of 1.2 kV/mm, a capacitance of 50 μF and a resistance of 720Ω. The suspensions of bacterial cells after the electroporation are removed in the whole volume from the cuvettes and transferred to Sakaguchi flasks each containing 100 mL of modified Alexander medium, followed by incubation with shaking for 24 hours. Each 10-mL portion of the culture liquids is transferred to 100 mL of fresh Alexander medium containing 10 mg/L kanamycin, and these cultures are incubated with shaking. The incubation for 7 days gives the growth of microorganisms until it can be confirmed by visual observation (absorbance at 600 nm of about 0.1), at which time these cultures are diluted by a factor of $10^5$ to $10^7$ and spread on plates of modified Alexander medium containing 10 mg/L kanamycin. These plates are placed in an incubator at 28° C. for 10 days, giving colonies of transformants. The transformation efficiency is determined from the degree of colony formation for chimeric plasmids pAYS and pAYL.

EXAMPLE 7
(Second Example of Transformation of Ammonia Oxidizing Bacteria Using the Present Chimeric Plasmid)

Using the present chimeric plasmid as a vector, the transformation of ammonia oxidizing bacteria ENI-11 belonging to the genus Nitrosomonas was carried out. A liquid culture of ammonia oxidizing bacteria ENI-11 as a host organism was grown in a volume of 1000 mL according to Example 2, and the bacterial cells were collected by centrifugation and washed three times with sterilized water, which were then suspended in 0.4 mL of sterilized water. To this was added 0.01 mL of TE solution containing 1 µg of DNA of chimeric plasmid pAY3 obtained in Example 5, and the mixture was transferred in the whole volume to cuvettes with 2 mm gaps. A voltage was applied to the cuvettes using an apparatus for electroporation, Electro Cell Manipulator 600 available from BTX. The conditions of voltage application are set at a voltage of 1.2 kV/mm, a capacitance of 50 µF and a resistance of 720Ω. The suspension of bacterial cells after the electroporation was removed in the whole volume from the cuvettes and transferred to a Sakaguchi flask containing 100 mL of modified Alexander medium, followed by incubation with shaking for 24 hours. A 10-mL portion of the culture liquid was transferred to 100 mL of fresh Alexander medium containing 10 mg/L kanamycin, and the culture was incubated with shaking. The incubation for 7 days gave the growth of microorganisms until it could be confirmed by visual observation (absorbance at 600 nm of about 0.1), at which time the culture was diluted by a factor of $10^5$ to $10^7$ and spread on a plate of modified Alexander medium containing 10 mg/L kanamycin. The plate was placed in an incubator at 28° C. for 10 days to give colonies of transformants. The transformation efficiency of chimeric plasmid pAY3 was about 100–1000/µg DNA as calculated from the degree of colony formation. The transformant thus obtained was grown in a modified Alexander medium containing 10 mg/L kanamycin, from which the plasmid DNA was extracted, and the plasmid structure was analyzed by restriction treatment and electrophoresis. As a result, DNA fragments were detected in sizes as calculated from the restriction map of plasmid pAY3, making it possible to confirm that chimeric plasmid pAY3 was recovered from the transformants. The DNA of chimeric plasmid pAY3 recovered from the transformant was used for the transformation of *Esherichia coli* MV1184 as a host organism by the competent sell method involving the calcium chloride treatment. A culture of the transformed *Esherichia coli* was prepared on an agar plate containing ampicillin (100 mg/L) to screen for transformants. According to the ordinary method for the preparation of *Esherichia coli* cultures, an overnight culture of the *Esherichia coli* transformant colonies obtained was prepared, from which the plasmid DNA was extracted, and the plasmid structure was analyzed by restriction treatment and electrophoresis. As a result, DNA fragments were detected in sizes as calculated from the restriction map of chimeric plasmid pAY3, so that the recovery of chimeric plasmid pAY3 from the *Esherichia coli* transformants was confirmed. From these facts, it was found that chimeric plasmid pAY3 can function as a shuttle vector.

Effects of the Invention

The present invention provides transformation vectors for carrying out gene manipulation in ammonia oxidizing bacteria.

What is claimed is:

1. An isolated and purified plasmid comprising the nucleotide sequence of SEQ ID NO: 1.

2. The plasmid according to claim 1, wherein said plasmid comprises about 1.8 kilobase pairs and is represented by the restriction map shown in FIG. 1.

3. An isolated and purified plasmid comprising the nucleotide sequence of SEQ ID NO: 2.

4. The plasmid according to claim 3, wherein said plasmid comprises about 1.9 kilobase pairs and is represented by restriction map shown in FIG. 2.

5. A transformant produced by transferring at least one plasmid according to any one of claims 1 to 4 into a host organism.

6. A method for detecting ammonium ions in an aqueous solution, comprising the steps of:

obtaining a transformant by transferring into ammonia oxidizing bacteria a plasmid according to any one of claims 1 to 4 into which a luminescent organism derived nucleic acid sequence coding for a protein associated with bioluminescence has been inserted;

contacting said transformant with both a sample aqueous solution and a substrate for the bioluminescence; and measuring the bioluminescence of said transformant.

* * * * *

UNITED STATES PATENT AND TRADEMARK OFFICE
CERTIFICATE OF CORRECTION

PATENT NO. : 6,350,577 B1
DATED : February 26, 2002
INVENTOR(S) : Hisao Ohtake et al.

It is certified that error appears in the above-identified patent and that said Letters Patent is hereby corrected as shown below:

<u>Title page,</u>
Item [73], Assignee, change "Sumitomo Chemical Co., Ltd., Osaka (JP)" to
-- Sumitomo Chemical Company, Limited, Osaka (JP) --.

Signed and Sealed this

Second Day of July, 2002

Attest:

Attesting Officer

JAMES E. ROGAN
*Director of the United States Patent and Trademark Office*